US012626811B2

(12) United States Patent
Tamir

(10) Patent No.: US 12,626,811 B2
(45) Date of Patent: May 12, 2026

(54) SYSTEM AND METHOD FOR AI-BASED PRIORITIZATION OF PATIENTS

(71) Applicant: Lior Tamir, San Mateo, CA (US)

(72) Inventor: Lior Tamir, San Mateo, CA (US)

( * ) Notice: Subject to any disclaimer, the term of this patent is extended or adjusted under 35 U.S.C. 154(b) by 219 days.

(21) Appl. No.: 18/732,973

(22) Filed: Jun. 4, 2024

(65) Prior Publication Data

US 2026/0038672 A1     Feb. 5, 2026

(51) Int. Cl.
| | |
|---|---|
| *G16H 40/20* | (2018.01) |
| *G16H 10/60* | (2018.01) |
| *G16H 15/00* | (2018.01) |
| *G16H 20/40* | (2018.01) |

(52) U.S. Cl.
CPC ............. *G16H 40/20* (2018.01); *G16H 10/60* (2018.01); *G16H 15/00* (2018.01); *G16H 20/40* (2018.01)

(58) Field of Classification Search
CPC ........ G16H 40/20; G16H 20/40; G16H 10/60; G16H 15/00
See application file for complete search history.

(56) References Cited

U.S. PATENT DOCUMENTS

| | | | | | |
|---|---|---|---|---|---|
| 8,086,491 | B1 * | 12/2011 | Matz | .................. | G06Q 30/0269 |
| | | | | | 705/14.66 |
| 8,670,998 | B2 * | 3/2014 | Bertha | ................... | H04W 4/029 |
| | | | | | 705/3 |
| 8,843,394 | B2 * | 9/2014 | Cao | .................... | G06Q 30/0255 |
| | | | | | 705/14.66 |
| 10,468,140 | B2 * | 11/2019 | Wright | .................. | G16H 20/60 |
| 10,735,268 | B2 * | 8/2020 | Strom | ................. | H04L 43/0882 |
| 10,905,327 | B2 * | 2/2021 | Whiting | ................ | G16H 10/60 |
| 11,023,856 | B2 * | 6/2021 | Laster | ................ | G06Q 10/0875 |

(Continued)

OTHER PUBLICATIONS

Jafri, Elsevier, 2022, Chapter 4.*
Hassija, Elsevier, 2022, pp. 1-10.*

*Primary Examiner* — Michael I Ezewoko
(74) *Attorney, Agent, or Firm* — The Rapacke Law Group, P.A.

(57) ABSTRACT

A system for an automated dental patient prioritization and treatment processing based on dental patient-related data, including a processor of a dental patient processing server node configured to host a machine learning (ML) module and connected to an office manager-entity node and to at least one dentist entity node over a network and a memory on which are stored machine-readable instructions that when executed by the processor, cause the processor to: acquire a dental patient report including a list of dental procedures prescribed to a dental patient from the office manager-entity node; parse the dental patient report a to derive a plurality of key ordered features; query a local dental-patient's database to retrieve local historical dental-patients'-related data based on the plurality of the key ordered features; generate at least one feature vector based on the plurality of the key ordered features and the local historical dental patients'-related data; and provide the at least one feature vector to the ML module configured to generate a predictive model for producing at least one dental-patient processing recommendation parameter; and generate at least one procedure performance recommendation and dental patient prioritization based on the at least one dental-patient processing recommendation parameter.

16 Claims, 7 Drawing Sheets

(56) References Cited

U.S. PATENT DOCUMENTS

| | | | |
|---|---|---|---|
| 11,257,587 B1* | 2/2022 | D'Angelo | A61B 5/0022 |
| 11,476,002 B2* | 10/2022 | Shaw | G16H 15/00 |
| 11,972,860 B2* | 4/2024 | Tran | G06Q 30/04 |
| 11,991,046 B2* | 5/2024 | Wu | H04L 41/22 |
| 12,087,434 B2* | 9/2024 | Xu | G16H 50/70 |
| 2004/0236608 A1* | 11/2004 | Ruggio | G16H 10/20 |
| | | | 705/2 |
| 2005/0022114 A1* | 1/2005 | Shanahan | G06F 21/10 |
| | | | 715/234 |
| 2005/0060199 A1* | 3/2005 | Siegel | G16H 10/60 |
| | | | 600/300 |
| 2005/0149359 A1* | 7/2005 | Steinberg | G16H 50/20 |
| | | | 705/2 |
| 2007/0033072 A1* | 2/2007 | Bildirici | G09B 19/00 |
| | | | 434/262 |
| 2007/0050257 A1* | 3/2007 | Fine | G06Q 30/02 |
| | | | 705/14.56 |
| 2008/0046562 A1* | 2/2008 | Butler | G06F 16/958 |
| | | | 709/224 |
| 2009/0037216 A1* | 2/2009 | Bluemler | G16H 40/63 |
| | | | 705/2 |
| 2009/0076914 A1* | 3/2009 | Coueignoux | G06Q 30/02 |
| | | | 705/14.69 |
| 2009/0254376 A1* | 10/2009 | Martinez | G16H 10/60 |
| | | | 705/30 |
| 2011/0166880 A1* | 7/2011 | Keynan | G16H 15/00 |
| | | | 705/2 |
| 2011/0292832 A1* | 12/2011 | Bottari | H04L 12/4013 |
| | | | 370/254 |
| 2011/0313847 A1* | 12/2011 | Cao | G06Q 30/0244 |
| | | | 705/14.43 |
| 2012/0140671 A1* | 6/2012 | Bukofser | H04L 41/12 |
| | | | 370/253 |
| 2012/0259657 A1* | 10/2012 | Keynan | G16Z 99/00 |
| | | | 705/2 |
| 2012/0272134 A1* | 10/2012 | Steelberg | G06F 3/0484 |
| | | | 715/234 |
| 2013/0144637 A1* | 6/2013 | Bertha | G06Q 30/0207 |
| | | | 705/2 |
| 2014/0143304 A1* | 5/2014 | Hegarty | H04L 67/535 |
| | | | 709/203 |
| 2014/0249849 A1* | 9/2014 | Khare | G16H 10/60 |
| | | | 705/3 |
| 2015/0220941 A1* | 8/2015 | Tamir | G06Q 30/0201 |
| | | | 705/7.29 |
| 2016/0342581 A1* | 11/2016 | Delgado | G06F 40/117 |
| 2017/0061091 A1* | 3/2017 | McElhinney | G16H 10/60 |
| 2017/0331687 A1* | 11/2017 | Crickett | H04L 41/12 |
| 2018/0309636 A1* | 10/2018 | Strom | H04L 43/08 |
| 2019/0035499 A1* | 1/2019 | Daya | G16H 80/00 |
| 2020/0328946 A1* | 10/2020 | Strom | H04L 45/02 |
| 2020/0411149 A1* | 12/2020 | Chung | A61B 5/6892 |
| 2021/0058446 A1* | 2/2021 | Qiu | G06F 16/9538 |
| 2021/0073312 A1* | 3/2021 | Anno | G06F 16/90328 |
| 2021/0097045 A1* | 4/2021 | Agrawal | G06F 16/22 |
| 2021/0110897 A1* | 4/2021 | Ginsburg | G16H 10/60 |
| 2021/0134414 A1* | 5/2021 | Pollack | G16H 50/70 |
| 2021/0174925 A1* | 6/2021 | Daya | G16H 40/67 |
| 2021/0296000 A1* | 9/2021 | Shaw | G06Q 30/0202 |
| 2021/0398668 A1* | 12/2021 | Chock | G06F 3/0482 |
| 2022/0210024 A1* | 6/2022 | Li | H04L 41/12 |
| 2023/0056899 A1* | 2/2023 | Blanchard | G16H 10/60 |
| 2023/0170065 A1* | 6/2023 | De Vries | G16H 50/30 |
| | | | 705/2 |
| 2023/0231773 A1* | 7/2023 | Wu | H04L 41/22 |
| | | | 709/220 |
| 2023/0343432 A1* | 10/2023 | Daya | G16H 50/30 |
| 2024/0073171 A1* | 2/2024 | Mitra | H04L 51/216 |
| 2024/0105319 A1* | 3/2024 | Ahmed | G16H 10/20 |
| 2024/0113944 A1* | 4/2024 | Wu | H04L 41/12 |
| 2024/0154855 A1* | 5/2024 | Jayaram | H04L 41/12 |
| 2025/0220488 A1* | 7/2025 | Ziv | H04W 56/002 |

* cited by examiner

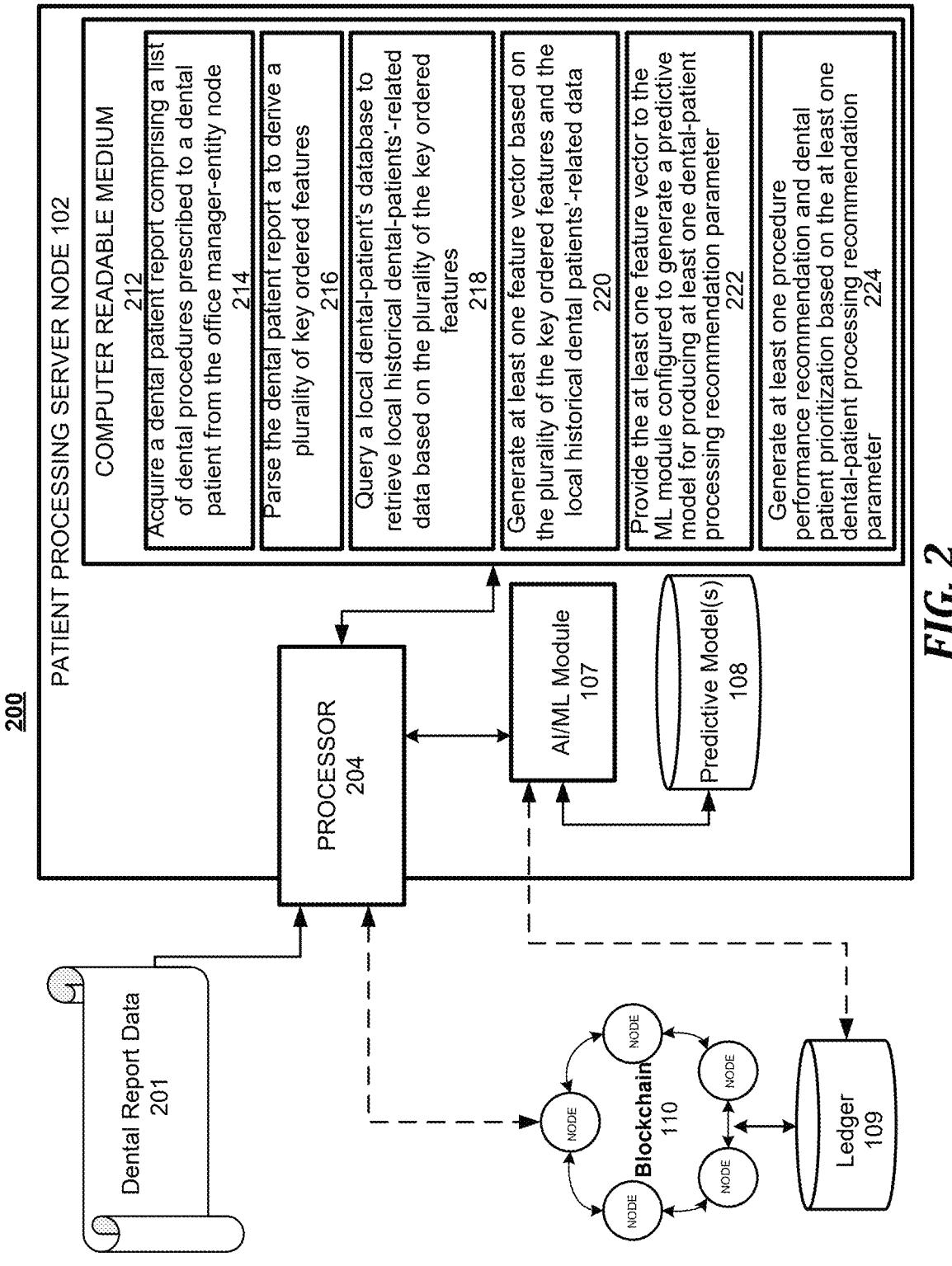

200

PATIENT PROCESSING SERVER NODE 102

COMPUTER READABLE MEDIUM 212

Acquire a dental patient report comprising a list of dental procedures prescribed to a dental patient from the office manager-entity node 214

Parse the dental patient report a to derive a plurality of key ordered features 216

Query a local dental-patient's database to retrieve local historical dental-patients'-related data based on the plurality of the key ordered features 218

Generate at least one feature vector based on the plurality of the key ordered features and the local historical dental patients'-related data 220

Provide the at least one feature vector to the ML module configured to generate a predictive model for producing at least one dental-patient processing recommendation parameter 222

Generate at least one procedure performance recommendation and dental patient prioritization based on the at least one dental-patient processing recommendation parameter 224

PROCESSOR 204

AI/ML Module 107

Predictive Model(s) 108

Dental Report Data 201

NODE

NODE

NODE

NODE

NODE

Blockchain 110

Ledger 109

*FIG. 2*

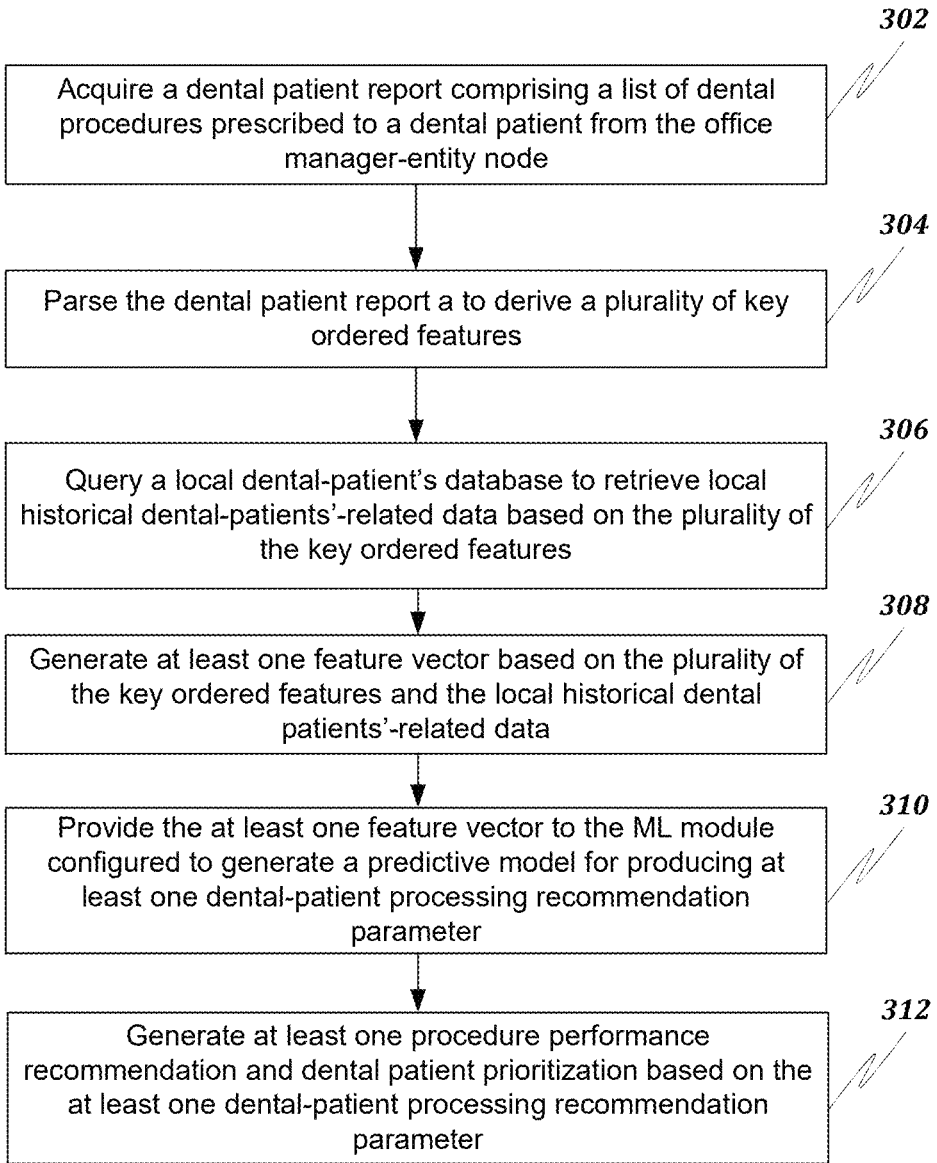

<u>300</u>

*302*

Acquire a dental patient report comprising a list of dental procedures prescribed to a dental patient from the office manager-entity node

*304*

Parse the dental patient report a to derive a plurality of key ordered features

*306*

Query a local dental-patient's database to retrieve local historical dental-patients'-related data based on the plurality of the key ordered features

*308*

Generate at least one feature vector based on the plurality of the key ordered features and the local historical dental patients'-related data

*310*

Provide the at least one feature vector to the ML module configured to generate a predictive model for producing at least one dental-patient processing recommendation parameter

*312*

Generate at least one procedure performance recommendation and dental patient prioritization based on the at least one dental-patient processing recommendation parameter

*FIG. 3A*

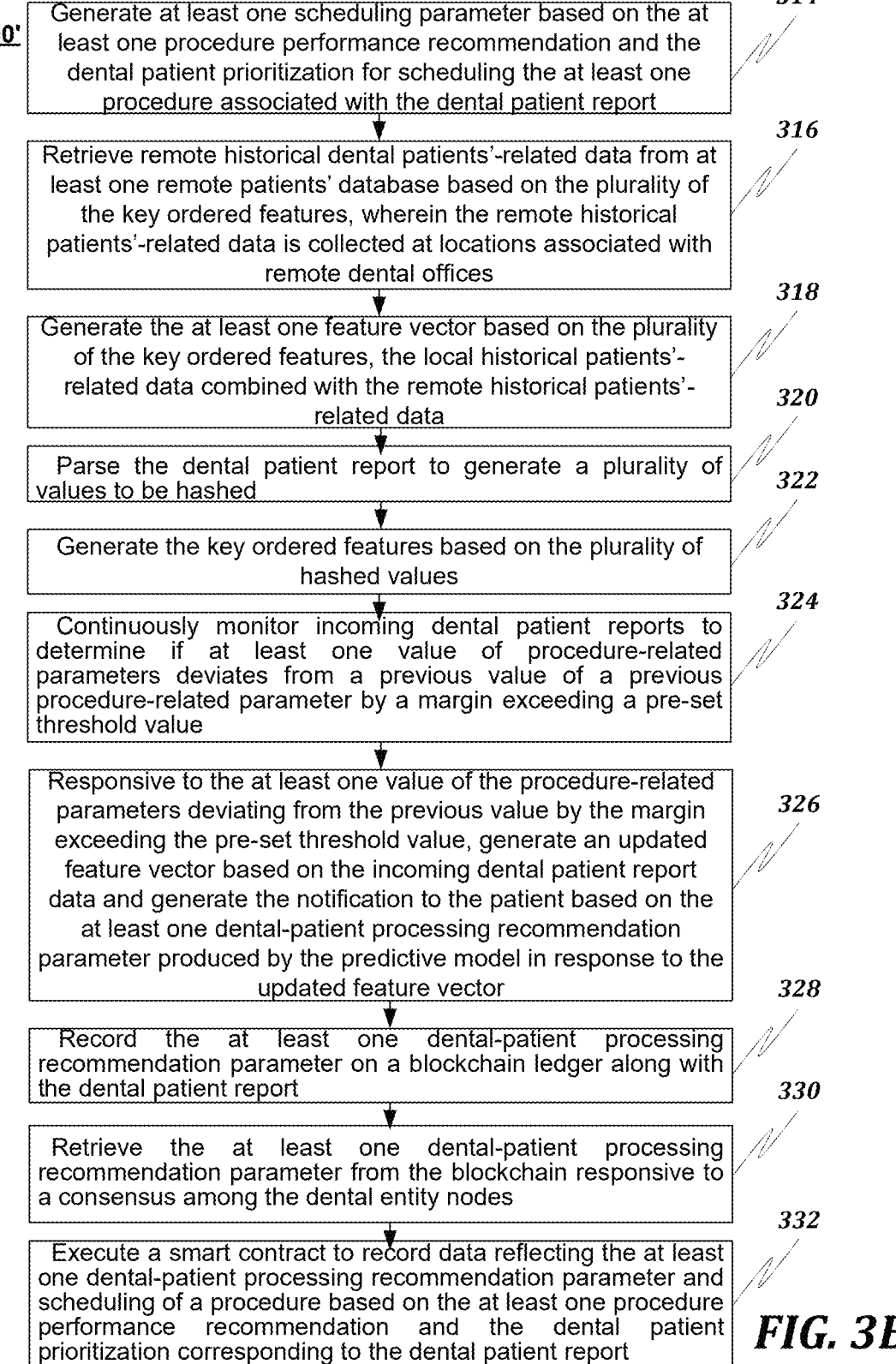

300'

*314*

Generate at least one scheduling parameter based on the at least one procedure performance recommendation and the dental patient prioritization for scheduling the at least one procedure associated with the dental patient report

*316*

Retrieve remote historical dental patients'-related data from at least one remote patients' database based on the plurality of the key ordered features, wherein the remote historical patients'-related data is collected at locations associated with remote dental offices

*318*

Generate the at least one feature vector based on the plurality of the key ordered features, the local historical patients'-related data combined with the remote historical patients'-related data

*320*

Parse the dental patient report to generate a plurality of values to be hashed

*322*

Generate the key ordered features based on the plurality of hashed values

*324*

Continuously monitor incoming dental patient reports to determine if at least one value of procedure-related parameters deviates from a previous value of a previous procedure-related parameter by a margin exceeding a pre-set threshold value

*326*

Responsive to the at least one value of the procedure-related parameters deviating from the previous value by the margin exceeding the pre-set threshold value, generate an updated feature vector based on the incoming dental patient report data and generate the notification to the patient based on the at least one dental-patient processing recommendation parameter produced by the predictive model in response to the updated feature vector

*328*

Record the at least one dental-patient processing recommendation parameter on a blockchain ledger along with the dental patient report

*330*

Retrieve the at least one dental-patient processing recommendation parameter from the blockchain responsive to a consensus among the dental entity nodes

*332*

Execute a smart contract to record data reflecting the at least one dental-patient processing recommendation parameter and scheduling of a procedure based on the at least one procedure performance recommendation and the dental patient prioritization corresponding to the dental patient report

*FIG. 3B*

400
402
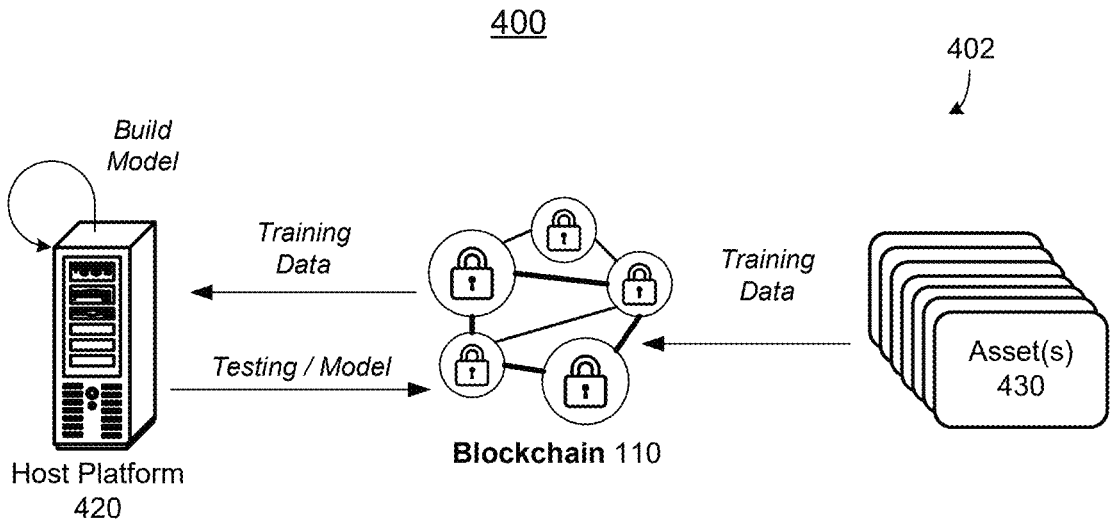
*Build Model*
Training Data
Testing / Model
Blockchain 110
Training Data
Asset(s) 430
Host Platform 420
404
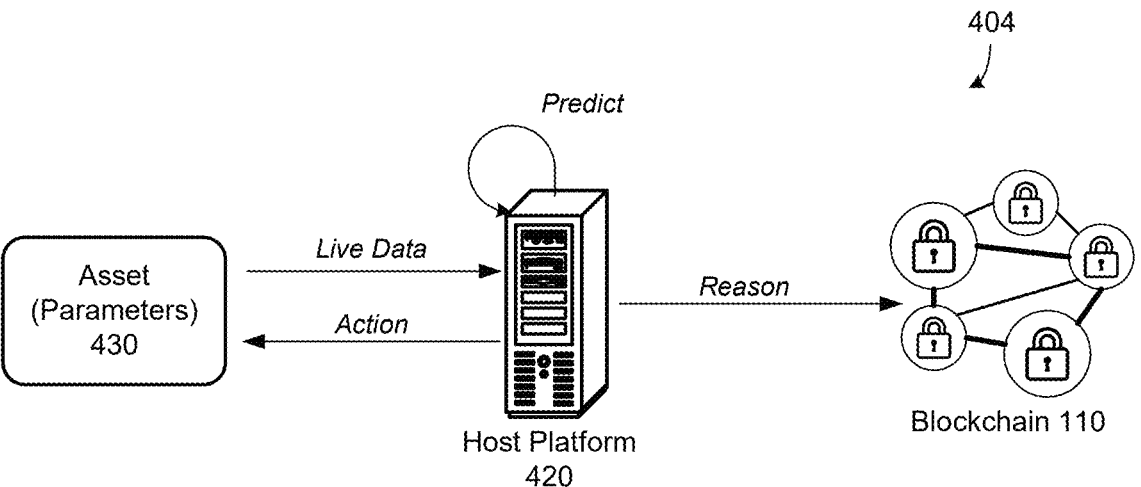
*Predict*
Asset (Parameters) 430
Live Data
Action
Reason
Host Platform 420
Blockchain 110
*FIG. 4*

SYSTEM AND METHOD FOR AI-BASED PRIORITIZATION OF PATIENTS

FIELD OF DISCLOSURE

The present disclosure generally relates to determining and scheduling dental procedures, and more particularly, to an AI-based automated system for real-time selection, prioritization and scheduling of dental procedures based on predictive analytics of dental patients'-related historical heuristic data.

BACKGROUND

The process of scheduling dental appointments after the initial consultation often becomes time and resource consuming as dental patients try to postpone or even avoid certain procedures.

While dental offices may use scheduling applications, these patient management software does not assist in the patients scheduling and actually going through with the dental procedures after the initial screening is done at the dental appointment and a report with a list of the procedures is generated. While the report is there and the patient is placed on the list for scheduling, many patients require multiple contacts (calls, emails, etc.) to schedule an appointment for the procedure according to the report because of the fear, financial considerations and general procrastinations that are very typical in dental industry. Many dental patients never follow through with the prescribed procedures at all. This way many patients are lost or require multiple notifications that cost dental business losses in time and revenues.

What is needed is an automated method to prioritize dental patients (and corresponding procedures) based on some collected data from the patients of the same type—i.e., gender, age. race, locations, assigned procedure, insurance type, etc., etc. For example, a 19-year-old male patient may be likely to come back for filling or cleaning, but is initially less likely to deal with root canal and subsequent crown. The 19-year-old male patient may be best reached over SMS and will not respond to phone calls or emails, etc. However, the existing scheduling and healthcare management applications do not take any of these scenarios into consideration and do not improve the dental procedure scheduling statistics.

Accordingly, a system and method for automated real-time selection, prioritization and scheduling of dental procedures based on predictive analytics of dental patients'-related historical heuristic data are desired.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

One embodiment of the present disclosure provides a system for an automated dental patient prioritization and treatment processing based on dental patient-related data, including a processor of a dental patient processing server node configured to host a machine learning (ML) module and connected to an office manager-entity node and to at least one dentist entity node over a network and a memory on which are stored machine-readable instructions that when executed by the processor, cause the processor to: acquire a dental patient report including a list of dental procedures prescribed to a dental patient from the office manager-entity node; parse the dental patient report a to derive a plurality of key ordered features; query a local dental-patient's database to retrieve local historical dental-patients'-related data based on the plurality of the key ordered features; generate at least one feature vector based on the plurality of the key ordered features and the local historical dental patients'-related data; and provide the at least one feature vector to the ML module configured to generate a predictive model for producing at least one dental-patient processing recommendation parameter; and generate at least one procedure performance recommendation and dental patient prioritization based on the at least one dental-patient processing recommendation parameter.

Another embodiment of the present disclosure provides a method that includes one or more of: acquiring a dental patient report including a list of dental procedures prescribed to a dental patient from the office manager-entity node; parsing the dental patient report a to derive a plurality of key ordered features; querying a local dental-patient's database to retrieve local historical dental-patients'-related data based on the plurality of the key ordered features; generating at least one feature vector based on the plurality of the key ordered features and the local historical dental patients'-related data; and providing the at least one feature vector to the ML module configured to generate a predictive model for producing at least one dental-patient processing recommendation parameter; and generating at least one procedure performance recommendation and dental patient prioritization based on the at least one dental-patient processing recommendation parameter.

Another embodiment of the present disclosure provides a computer-readable medium including instructions for acquiring a dental patient report including a list of dental procedures prescribed to a dental patient from the office manager-entity node; parsing the dental patient report a to derive a plurality of key ordered features; querying a local dental-patient's database to retrieve local historical dental-patients'-related data based on the plurality of the key ordered features; generating at least one feature vector based on the plurality of the key ordered features and the local historical dental patients'-related data; and providing the at least one feature vector to the ML module configured to generate a predictive model for producing at least one dental-patient processing recommendation parameter; and generating at least one procedure performance recommendation and dental patient prioritization based on the at least one dental-patient processing recommendation parameter.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings:

FIG. 2 illustrates a network diagram of a system including detailed features of a dental Patient Processing server (PPS) node consistent with the present disclosure;

FIG. 3A illustrates a flowchart of a method for AI-based automated predictive analytics of dental patients'-related data consistent with the present disclosure;

FIG. 3B illustrates a further flow chart of a method for AI-based automated predictive analytics of dental patients'-related data consistent with the present disclosure;

FIG. 4 illustrates deployment of a machine learning model for prediction of dental procedure parameters using blockchain assets consistent with the present disclosure;

DETAILED DESCRIPTION

Figure 1A:
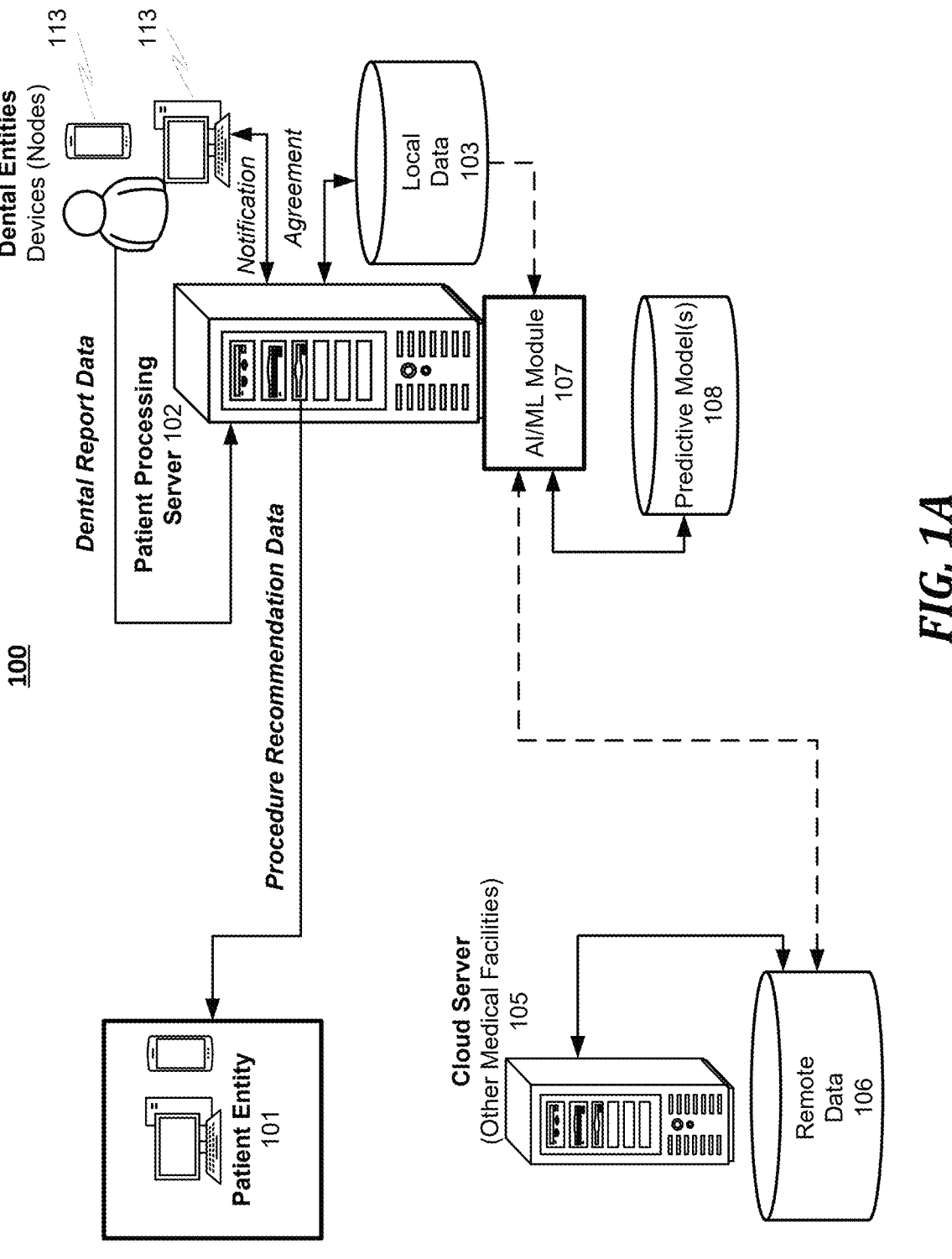
FIG. 1A illustrates a network diagram of a system for AI-based automated predictive analytics of dental patients'-related data, consistent with the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of processing job applicants, embodiments of the present disclosure are not limited to use only in this context.

The present disclosure provides a system, method and computer-readable medium for AI-based automated predictive analytics of dental patients'-related data.

In one embodiment of the present disclosure, the system provides for AI and machine learning (ML)-generated list of dental procedure recommendation parameters to be used for analysis and generation of procedure-related notifications to the patients. In one embodiment, an automated decision model may be generated to provide for procedure-related parameters associated with a dental patients' current status, past procedure-related behavior based on previous dentist' feedback, medical reports, social media accounts of the patient, etc.

The automated notification decision model may use historical dental patients' data collected at the current locations (i.e., a dental office or other medical site) and at other medical facilities of the same type located within a certain range from the current location or even located globally. The relevant dental patient's data may include data related to other dental patients having the same parameters such as diagnosis and/or dental procedures, age, race, gender, language, preferred procedure conditions or locations, etc.

In one disclosed embodiment, the AI/ML technology may be combined with a blockchain technology for secure use of the dental patient-related data. The disclosed embodiment may produce a detailed safety or success rates score on the successful procedure likelihood for the given patient based on collected patients' behavioral data. This allows for direct reporting on a trust level of the given patient to the dental management entities (i.e., dentists, doctors, hospitals, emergency services, etc.). In one embodiment, the dental entities may be connected to the Patient Processing server (PPS) node over a blockchain network to achieve a consensus prior to executing a transaction to release the patient data or the patient procedure-related conditions based on the patient-related parameters. The patient parameters may be represented as hashed data. The system may use hashed data to schedule the dental procedures based on the patient being on-boarded to the system via a blockchain network.

In one embodiment, the disclosed system may relate to a SaaS platform that matches the dental patients with the procedures indicated in the patient report produced by the dentist. The dental patients may receive AI-generated recommendations for scheduling the procedures based on their hash values or parameters. The PPS node may automatically choose the dental procedure(s) from the report that best fits the patients parameters derived from the patients' historical data.

When more than one patient is matched to a procedure at the same time slot, the system may have an option to review the patients' profiles and pick or choose which matched patients should get notified bases on the predictive parameters produced by the AI. The patient may be notified of the available procedure over a blockchain network. Once consensus is received from the patient(s), the dentist office manager entity is notified and may execute a blockchain transaction for assigning the patient to the dental procedure at the available time slot.

The disclosed process, advantageously, eliminates the need for dental office personnel to constantly call the patients by enabling the patients and the dental procedure for the patient's dental report to be automatically matched directly on a granular level based on the AI-based predictive analysis and recommendations. This process includes scheduling mechanism coupled with a secure communications chat channel (implemented over a blockchain network) which supports both parties to set, negotiate, and agree on the procedure, times and terms of procedure performance with each other using a dynamic automated function.

FIG. 1A illustrates a network diagram of a system for AI-based automated predictive analytics of dental patients'-related data, consistent with the present disclosure.

As discussed above, an AI/ML module may produce predictive parameters for processing (contacting, scheduling, etc.) the dental patients based on the current patient data and the patient report and based also on the collected data from other patients of the same type used in training of the predictive models. As such, based on the predictive parameters, the dental patients may be prioritized to be contacted and scheduled for the procedure(s). In this case, the scheduled procedure may not be the most important (must do one), but rather the one the patient is most likely to agree to schedule and actually go through with. The patient's report is updated after the procedure is done and is run through the AI module again to produce new patient processing parameters used to determine the next most likely procedure—not the most important one, perhaps, but the most likely to be accepted. The disclosed automated AI-based approach will, advantageously, reduce lost revenues and improve patients' responsiveness, because the patient is always offered something he or she is likely to agree to have done based on fine-tuned training models.

Referring to FIG. 1A, the example network 100 includes the Patient Processing server (PPS) node 102 connected to a cloud server node(s) 105 over a network. The PPS node 102 is configured to host an AI/ML module 107. The PPS node 102 may receive patient dental report data from a dental entity 113. The patient dental report data may have a list of procedures prescribed to the dental patient based on the initial screening appointment or based in the current latest appointment. In one embodiment, the patient dental report data may be processed by the PPS node 102 to parse out the parameters or to generate hash values from the procedure descriptions.

The PPS node 102 may query a local dental patients' database for the historical local patients' data 103 associated with the current patient dental report data. The PPS node 102 may acquire relevant remote patients' data 106 from a remote database residing on a cloud server 105. The remote patients' data 106 may be collected from other dental offices entities (or medical facilities). The remote patients' data 106 may be collected from patients that had the same (or similar) diagnosis or recommended procedures, age, gender, race, language, procedure preferences, locations, etc. as the local patients' who are associated with the current patient dental report data.

The PPS node 102 may generate a feature vector or classifier based on the patient dental report and the collected patients' data (i.e., pre-stored local data 103 and remote data 106). The PPS node 102 may ingest the feature vector data into an AI/ML module 107. The AI/ML module 107 may generate a predictive model(s) 108 based on the feature vector data to predict procedure-related scheduling parameters for automatically generating a notification(s) to be provided to patient entities 101. The procedure-related scheduling parameters may be further analyzed by the PPS node 102 prior to generation of the notification(s). In one embodiment, the procedure-related scheduling parameters may be used for adjustment of the dental office schedule based on availability of the selected (i.e., matched) patients.

Figure 1B:
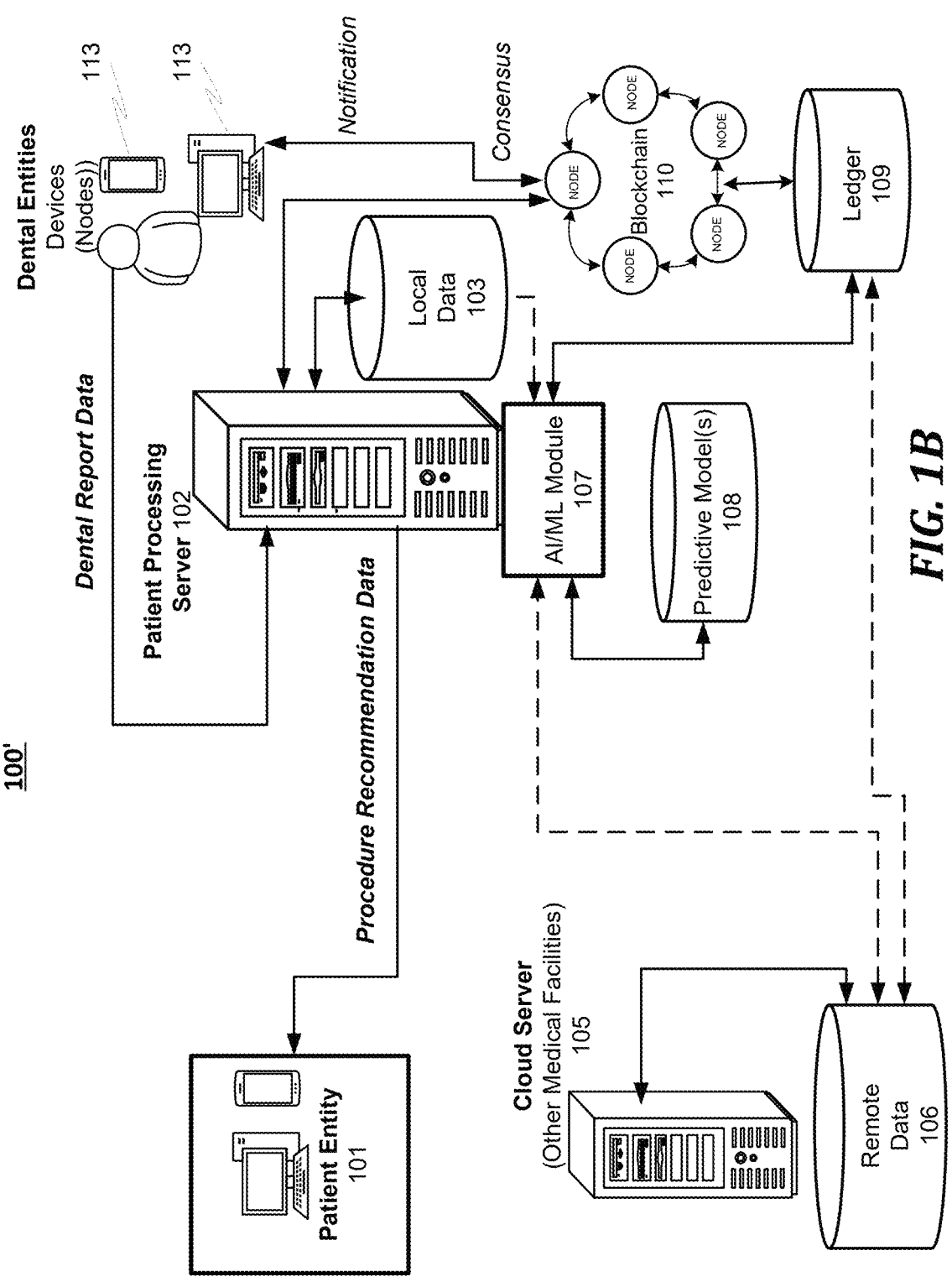
FIG. 1B illustrates a network diagram of a system for AI-based automated predictive analytics of dental patients'-related data and receiving procedure consensus over a blockchain consistent with the present disclosure.

FIG. 1B illustrates a network diagram of a system for AI-based automated predictive analytics of dental patients'-related data and receiving procedure consensus over a blockchain consistent with the present disclosure.

Referring to FIG. 1B, the example network 100' includes the Patient Processing server (PPS) node 102 connected to a cloud server node(s) 105 over a network. The PPS node 102 is configured to host an AI/ML module 107. The PPS node 102 may receive patient dental report data from a dental entity 113. The patient dental report data may have a list of procedures prescribed to the dental patient based on the initial screening appointment or based in the current latest appointment. In one embodiment, the patient dental report data may be processed by the PPS node 102 to parse out the parameters or to generate hash values from the procedure descriptions.

The PPS node 102 may query a local dental patients' database for the historical local patients' data 103 associated with the current patient dental report data. The PPS node 102 may acquire relevant remote patients' data 106 from a remote database residing on a cloud server 105. The remote patients' data 106 may be collected from other dental offices entities (or medical facilities). The remote patients' data 106 may be collected from patients that had the same (or similar) diagnosis or recommended procedures, age, gender, race, language, procedure preferences, locations, etc. as the local patients' who are associated with the current patient dental report data.

The PPS node 102 may generate a feature vector or classifier based on the patient dental report and the collected patients' data (i.e., pre-stored local data 103 and remote data 106). The PPS node 102 may ingest the feature vector data into an AI/ML module 107. The AI/ML module 107 may generate a predictive model(s) 108 based on the feature vector data to predict procedure-related scheduling parameters for automatically generating a notification(s) to be provided to patient entities 101. The procedure-related scheduling parameters may be further analyzed by the PPS node 102 prior to generation of the notification(s). In one embodiment, the procedure-related scheduling parameters may be used for adjustment of the dental office schedule based on availability of the selected (i.e., matched) patients.

In one embodiment, the PPS node 102 may receive the predicted procedure-related parameters from a permissioned blockchain 110 ledger 109 based on a consensus from the patients' entities (devices) 101 confirming, for example, dates and times for the dental procedure to be scheduled. Additionally, confidential historical patient-related information and previous patients'-related parameters may also be acquired from the permissioned blockchain 110. The newly acquired patient-related data with corresponding predicted procedure-related parameters data may be also recorded on the ledger 109 of the blockchain 110 so it can be used as training data for the predictive model(s) 108. In this implementation the PSS node 102, the cloud server 105, the patient entity devices 101 and dental entities(s) 113 (i.e., dentists, nurses, schedulers, etc.) may serve as blockchain 110 peer nodes. In one embodiment, local patients' data 103 and remote patients' data 106 may be duplicated on the blockchain ledger 109 for higher security of storage.

The AI/ML module 107 may generate a predictive model(s) 108 to predict the procedure-related parameters for the patients in response to the specific relevant pre-stored patients'-related data acquired from the blockchain 110 ledger 109. This way, the current procedure-related parameters may be predicted based not only on the current patient's report data and current patients'-related data, but also based on the previously collected heuristics and patients'-related data associated with the given patient's report data or current procedure-related scheduling parameters predicted based by the AI/ML module 107. As one additional improvement, the patient report data can be recorded on the blockchain for privacy and the patient reports may be implemented as NFTs or other digital assets, etc.

FIG. 2 illustrates a network diagram of a system including detailed features of a dental Patient Processing server (PPS) node consistent with the present disclosure.

Referring to FIG. 2, the example network 200 includes the PPS node 102 connected to dental entities device(s) 113 to receive patient dental report data 201. The PPS node 102 is configured to host an AI/ML module 107. As discussed above with respect to FIGS. 1A-B, the PPS node 102 may receive patient dental report data 201 provided by the dental entities device(s) 113 (FIG. 1A) and pre-stored patients' data retrieved from local and remote databases. As discussed above, the pre-stored patients' data may be retrieved from the ledger 109 of the blockchain 110.

The AI/ML module 107 may generate a predictive model (s) 108 based on the received patient dental report data 201 and the patients'-related data provided by the PPS node 102. As discussed above, the AI/ML module 107 may provide predictive outputs data in a form of procedure-related scheduling parameters for automatic generation of notifications for the patients or for adjusting the procedure schedule for the patients. In one embodiment, the PPS node 102 may process the predictive outputs data received from the AI/ML module 107 to generate the notification of a current risk assessment ranking pertaining to a particular matched patients and the dental procedure.

In one embodiment, the PPS node 102 may acquire patient dental reports data from the dental entities periodically in order to check if new notifications need to be generated or the procedure schedule needs to be reset. In another embodiment, the PPS node 102 may continually monitor patients'-related data acquired from databases/blockchain ledger and may detect a parameter that deviates from a previous recorded parameter (or from a median reading value) by a margin that exceeds a threshold value pre-set for this particular parameter. For example, if a patients' conditions change due to already performed procedures, this may cause a change in this patient's procedure recommendation parameters. As another non-limiting example, a change in patient's insurance or coverage may also cause critical changes in patient's procedure scheduling possibilities. Accordingly, once the threshold is met or exceeded by at least one parameter of the patient, the PPS node 102 may provide the currently acquired patient parameter to the AI/ML module 107 to generate a list of updated parameters based on the current patient's conditions and requirements.

While this example describes in detail only one PPS node 102, multiple such nodes may be connected to the network and to the blockchain 110. It should be understood that the PPS node 102 may include additional components and that some of the components described herein may be removed and/or modified without departing from a scope of the PPS node 102 disclosed herein. The PPS node 102 may be a computing device or a server computer, or the like, and may include a processor 204, which may be a semiconductor-based microprocessor, a central processing unit (CPU), an application specific integrated circuit (ASIC), a field-programmable gate array (FPGA), and/or another hardware device. Although a single processor 204 is depicted, it should be understood that the PPS node 102 may include multiple processors, multiple cores, or the like, without departing from the scope of the PPS node 102 system.

The PPS node 102 may also include a non-transitory computer readable medium 212 that may have stored thereon machine-readable instructions executable by the processor 204. Examples of the machine-readable instructions are shown as 214-224 and are further discussed below. Examples of the non-transitory computer readable medium 212 may include an electronic, magnetic, optical, or other physical storage device that contains or stores executable instructions. For example, the non-transitory computer readable medium 212 may be a Random-Access memory (RAM), an Electrically Erasable Programmable Read-Only Memory (EEPROM), a hard disk, an optical disc, or other type of storage device.

The processor 204 may fetch, decode, and execute the machine-readable instructions 214 to acquire a dental patient report comprising a list of dental procedures prescribed to a dental patient from the office manager-entity node. The processor 204 may fetch, decode, and execute the machine-readable instructions 216 to parse the dental patient report a to derive a plurality of key ordered features. The processor 204 may fetch, decode, and execute the machine-readable instructions 218 to query a local dental-patient's database to retrieve local historical dental-patients'-related data based on the plurality of the key ordered features. The processor 204 may fetch, decode, and execute the machine-readable instructions 220 to generate at least one feature vector based on the plurality of the key ordered features and the local historical dental patients'-related data.

The processor 204 may fetch, decode, and execute the machine-readable instructions 222 to provide the at least one feature vector to the ML module configured to generate a predictive model for producing at least one dental-patient processing recommendation parameter. The processor 204 may fetch, decode, and execute the machine-readable instructions 224 to generate at least one procedure performance recommendation and dental patient prioritization based on the at least one dental-patient processing recommendation parameter.

The permissioned blockchain 110 may be configured to use one or more smart contracts that manage transactions for multiple participating nodes and for recording the transactions on the ledger 109.

FIG. 3A illustrates a flowchart of a method for AI-based automated predictive analytics of dental patients'-related data consistent with the present disclosure.

Referring to FIG. 3A, the method 300 may include one or more of the steps described below. FIG. 3A illustrates a flow chart of an example method executed by the PPS 102 (see FIG. 2). It should be understood that method 300 depicted in FIG. 3A may include additional operations and that some of the operations described therein may be removed and/or modified without departing from the scope of the method 300. The description of the method 300 is also made with reference to the features depicted in FIG. 2 for purposes of illustration. Particularly, the processor 204 of the PPS node 102 may execute some or all of the operations included in the method 300.

With reference to FIG. 3A, at block 302, the processor 204 may acquire a dental patient report comprising a list of dental procedures prescribed to a dental patient from the office manager-entity node. At block 304, the processor 204 may parse the dental patient report a to derive a plurality of key ordered features. At block 306, the processor 204 may query a local dental-patient's database to retrieve local historical dental-patients'-related data based on the plurality of the key ordered features. At block 308, the processor 204 may generate at least one feature vector based on the plurality of the key ordered features and the local historical dental patients'-related data. At block 310, the processor 204 may provide the at least one feature vector to the ML module configured to generate a predictive model for producing at least one dental-patient processing recommendation parameter. At block 312, the processor 204 may generate at least one procedure performance recommendation and dental patient prioritization based on the at least one dental-patient processing recommendation parameter.

FIG. 3B illustrates a further flow chart of a method for AI-based automated predictive analytics of dental patients'-related data consistent with the present disclosure.

Referring to FIG. 3B, the method 300' may include one or more of the steps described below. FIG. 3B illustrates a flow chart of an example method executed by the PPS 102 (see FIG. 2). It should be understood that method 300' depicted in FIG. 3B may include additional operations and that some of the operations described therein may be removed and/or modified without departing from the scope of the method 300'. The description of the method 300' is also made with reference to the features depicted in FIG. 2 for purposes of illustration. Particularly, the processor 204 of the PPS 102 may execute some or all of the operations included in the method 300'.

With reference to FIG. 3B, at block 314, the processor 204 may generate at least one scheduling parameter based on the at least one procedure performance recommendation and the dental patient prioritization for scheduling the at least one procedure associated with the dental patient report. At block 316, the processor 204 may retrieve remote historical dental patients'-related data from at least one remote patients' database based on the plurality of the key ordered features, wherein the remote historical patients'-related data is collected at locations associated with remote dental offices. At block 318, the processor 204 may generate the at least one feature vector based on the plurality of the key ordered features, the local historical patients'-related data combined with the remote historical patients'-related data. At block 320, the processor 204 may parse the dental patient report to generate a plurality of values to be hashed.

At block 322, the processor 204 may generate the key ordered features based on the plurality of hashed values. At block 324, the processor 204 may continuously monitor incoming dental patient reports to determine if at least one value of procedure-related parameters deviates from a previous value of a previous procedure-related parameter by a margin exceeding a pre-set threshold value. At block 326, the processor 204 may, responsive to the at least one value of the procedure-related parameters deviating from the previous value by the margin exceeding the pre-set threshold value, generate an updated feature vector based on the incoming dental patient report data and generate the notification to the patient based on the at least one dental-patient processing recommendation parameter produced by the predictive model in response to the updated feature vector. At block 328, the processor 204 may record the at least one dental-patient processing recommendation parameter on a blockchain ledger along with the dental patient report. At block 330, the processor 204 may retrieve the at least one dental-patient processing recommendation parameter from the blockchain responsive to a consensus among the dental entity nodes. At block 332, the processor 204 may execute a smart contract to record data reflecting the at least one dental-patient processing recommendation parameter and scheduling of a procedure based on the at least one procedure performance recommendation and the dental patient prioritization corresponding to the dental patient report.

In one disclosed embodiment, the procedure-related parameters' model may be generated by the AI/ML module 107 that may use training data sets to improve accuracy of the prediction of the procedure-related parameters for the patients' entities 101 (FIG. 1A). The procedure-related parameters used in training data sets may be stored in a centralized local database (such as one used for storing local patients' data 103 depicted in FIG. 1A). In one embodiment, a neural network may be used in the AI/ML module 107 for procedure-related and scheduling parameters modeling and procedure scheduling predictions.

In another embodiment, the AI/ML module 107 may use a decentralized storage such as a blockchain 110 (see FIG. 1B) that is a distributed storage system, which includes multiple nodes that communicate with each other. The decentralized storage includes an append-only immutable data structure resembling a distributed ledger capable of maintaining records between mutually untrusted parties. The untrusted parties are referred to herein as peers or peer nodes. Each peer maintains a copy of the parameter(s) records and no single peer can modify the records without a consensus being reached among the distributed peers. For example, the peers 101, 113, 105 and 102 (FIG. 1B) may execute a consensus protocol to validate blockchain 110 storage transactions, group the storage transactions into blocks, and build a hash chain over the blocks. This process forms the ledger 109 by ordering the storage transactions, as is necessary, for consistency. In various embodiments, a permissioned and/or a permissionless blockchain can be used. In a public or permissionless blockchain, anyone can participate without a specific identity. Public blockchains can involve assets and use consensus based on various protocols such as Proof of Work (PoW). On the other hand, a permissioned blockchain provides secure interactions among a group of entities which share a common goal such as storing alert parameters for efficient monitoring of a patient, but which do not fully trust one another.

This application utilizes a permissioned (private) blockchain that operates arbitrary, programmable logic, tailored to a decentralized storage scheme and referred to as "smart contracts" or "chaincodes." In some cases, specialized chaincodes may exist for management functions and parameters which are referred to as system chaincodes. The application can further utilize smart contracts that are trusted distributed applications which leverage tamper-proof properties of the blockchain database and an underlying agreement between nodes, which is referred to as an endorsement or endorsement policy. Blockchain transactions associated with this application can be "endorsed" before being committed to the blockchain while transactions, which are not endorsed, are disregarded. An endorsement policy allows chaincodes to specify endorsers for a transaction in the form of a set of peer nodes that are necessary for endorsement. When a client sends the transaction to the peers specified in the endorsement policy, the transaction is executed to validate the transaction. After a validation, the transactions enter an ordering phase in which a consensus protocol is used to produce an ordered sequence of endorsed transactions grouped into blocks.

In the example depicted in FIG. 4, a host platform 420 (such as the PSS node 102) builds and deploys a machine learning model for predictive monitoring of assets 430. Here, the host platform 420 may be a cloud platform, an industrial server, a web server, a personal computer, a user device, and the like. Assets 430 can represent notifications or patients' procedure-related parameters. The blockchain 110 can be used to significantly improve both a training process 402 of the machine learning model and the procedure-related parameters' predictive process 405 based on a trained machine learning model. For example, in 402, rather than requiring a data scientist/engineer or other user to collect the data, historical data (heuristics—i.e., patient-related data) may be stored by the assets 430 themselves (or through an intermediary, not shown) on the blockchain 110.

This can significantly reduce the collection time needed by the host platform 420 when performing predictive model training. For example, using smart contracts, data can be directly and reliably transferred straight from its place of origin (e.g., from the dental entities 113 or from patients' databases 103 and 106) to the blockchain 110. By using the blockchain 110 to ensure the security and ownership of the collected data, smart contracts may directly send the data from the assets to the entities that use the data for building a machine learning model. This allows for sharing of data among the assets 430. The collected data may be stored in the blockchain 110 based on a consensus mechanism. The consensus mechanism pulls in (permissioned nodes) to ensure that the data being recorded is verified and accurate. The data recorded is time-stamped, cryptographically signed, and immutable. It is therefore auditable, transparent, and secure.

Furthermore, training of the machine learning model on the collected data may take rounds of refinement and testing by the host platform 420. Each round may be based on additional data or data that was not previously considered to help expand the knowledge of the machine learning model. In 402, the different training and testing steps (and the data associated therewith) may be stored on the blockchain 110 by the host platform 420. Each refinement of the machine learning model (e.g., changes in variables, weights, etc.) may be stored on the blockchain 110. This provides verifiable proof of how the model was trained and what data was used to train the model. Furthermore, when the host platform 420 has achieved a finally trained model, the resulting model itself may be stored on the blockchain 110.

After the model has been trained, it may be deployed to a live environment where it can make patient-related predictions/decisions based on the execution of the final trained machine learning model using the procedure-related parameters. In this example, data fed back from the asset 430 may be input into the machine learning model and may be used to make event predictions such as most optimal procedures and scheduling parameters for scheduling procedures according to the patient dental report. Determinations made by the execution of the machine learning model (e.g., notification or scheduling parameters, etc.) at the host platform 420 may be stored on the blockchain 110 to provide auditable/verifiable proof. As one non-limiting example, the machine learning model may predict a future change of a part of the asset 430 (the patient notification parameters and assessment of risk of procedure). The data behind this decision may be stored by the host platform 420 on the blockchain 110.

As discussed above, in one embodiment, the features and/or the actions described and/or depicted herein can occur on or with respect to the blockchain 110. The above embodiments of the present disclosure may be implemented in hardware, in a computer-readable instructions executed by a processor, in firmware, or in a combination of the above. The computer computer-readable instructions may be embodied on a computer-readable medium, such as a storage medium. For example, the computer computer-readable instructions may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative embodiment, the processor and the storage medium may reside as discrete components. For example, FIG. 5 illustrates an example computing device (e.g., a server node) 500, which may represent or be integrated in any of the above-described components, etc.

Figure 5:
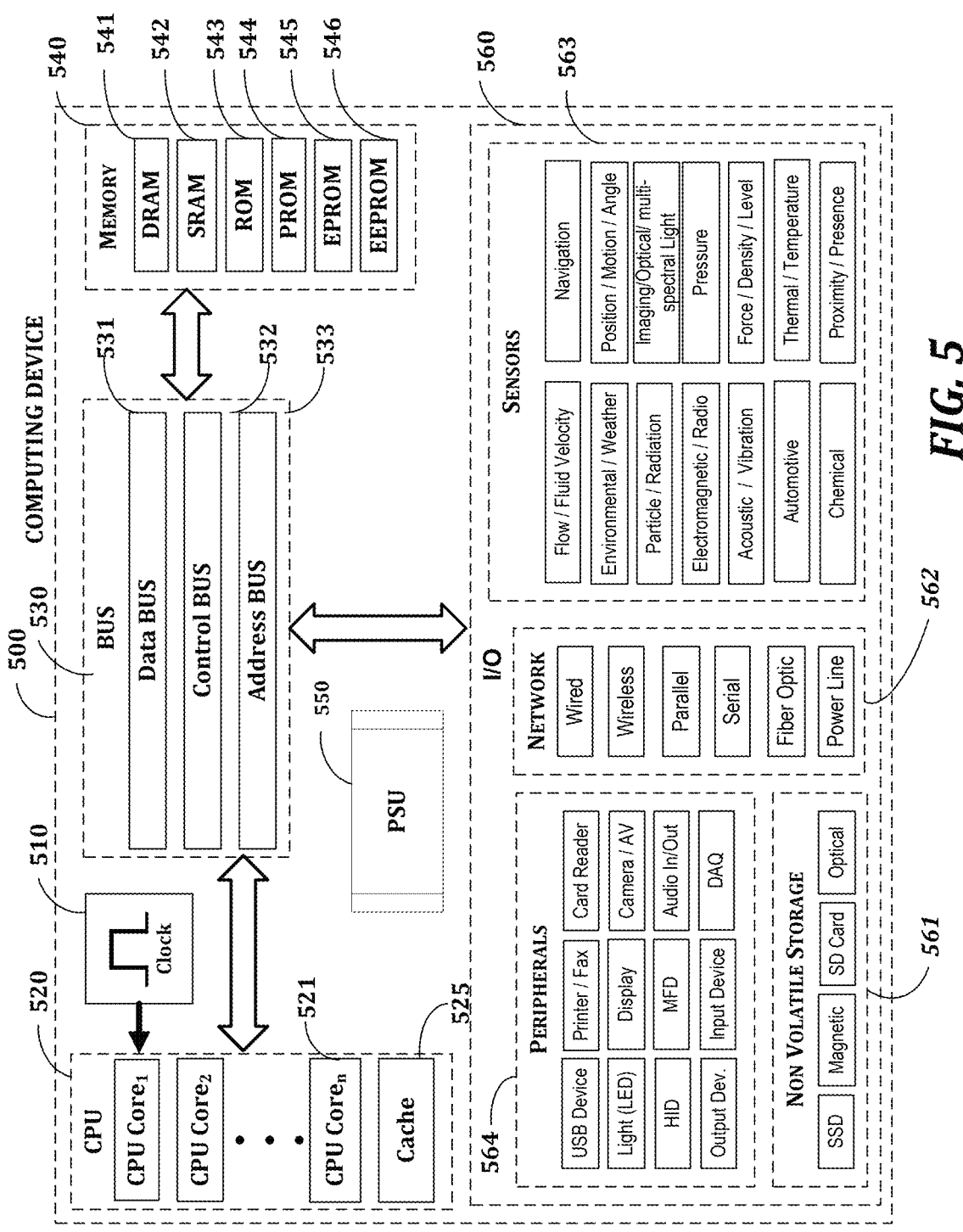
FIG. 5 illustrates a block diagram of a system including a computing device for performing the method of FIGS. 3A and 3B.

FIG. 5 illustrates a block diagram of a system including computing device 500. The computing device 500 may comprise, but not be limited to the following:

Mobile computing device, such as, but is not limited to, a laptop, a tablet, a smartphone, a drone, a wearable, an embedded device, a handheld device, an Arduino, an industrial device, or a remotely operable recording device;

A supercomputer, an exa-scale supercomputer, a mainframe, or a quantum computer;

A minicomputer, wherein the minicomputer computing device comprises, but is not limited to, an IBM AS500/iSeries/System I, A DEC VAX/PDP, a HP3000, a Honeywell-Bull DPS, a Texas Instruments TI-990, or a Wang Laboratories VS Series;

A microcomputer, wherein the microcomputer computing device comprises, but is not limited to, a server, wherein a server may be rack mounted, a workstation, an industrial device, a raspberry pi, a desktop, or an embedded device;

The PSS node 102 (see FIG. 2) may be hosted on a centralized server or on a cloud computing service. Although method 300 has been described to be performed by the PSS node 102 implemented on a computing device 500, it should be understood that, in some embodiments, different operations may be performed by a plurality of the computing devices 500 in operative communication at least one network.

Embodiments of the present disclosure may comprise a computing device having a central processing unit (CPU) 520, a bus 530, a memory unit 550, a power supply unit (PSU) 550, and one or more Input/Output (I/O) units. The CPU 520 coupled to the memory unit 550 and the plurality of I/O units 560 via the bus 530, all of which are powered by the PSU 550. It should be understood that, in some embodiments, each disclosed unit may actually be a plurality of such units for the purposes of redundancy, high availability, and/or performance. The combination of the presently disclosed units is configured to perform the stages any method disclosed herein.

Consistent with an embodiment of the disclosure, the aforementioned CPU 520, the bus 530, the memory unit 550, a PSU 550, and the plurality of I/O units 560 may be implemented in a computing device, such as computing device 500. Any suitable combination of hardware, software, or firmware may be used to implement the aforementioned units. For example, the CPU 520, the bus 530, and the memory unit 550 may be implemented with computing device 500 or any of other computing devices 500, in combination with computing device 500. The aforementioned system, device, and components are examples and other systems, devices, and components may comprise the aforementioned CPU 520, the bus 530, the memory unit 550, consistent with embodiments of the disclosure.

At least one computing device 500 may be embodied as any of the computing elements illustrated in all of the attached figures, including the design server node 102 (FIG. 2). A computing device 500 does not need to be electronic, nor even have a CPU 520, nor bus 530, nor memory unit 550. The definition of the computing device 500 to a person having ordinary skill in the art is "A device that computes, especially a programmable [usually] electronic machine that performs high-speed mathematical or logical operations or that assembles, stores, correlates, or otherwise processes information." Any device which processes information qualifies as a computing device 500, especially if the processing is purposeful.

With reference to FIG. 5, a system consistent with an embodiment of the disclosure may include a computing device, such as computing device 500. In a basic configuration, computing device 500 may include at least one clock module 510, at least one CPU 520, at least one bus 530, and at least one memory unit 550, at least one PSU 550, and at least one I/O 560 module, wherein I/O module may be comprised of, but not limited to a non-volatile storage sub-module 561, a communication sub-module 562, a sensors sub-module 563, and a peripherals sub-module 565.

A system consistent with an embodiment of the disclosure the computing device 500 may include the clock module 510 may be known to a person having ordinary skill in the art as a clock generator, which produces clock signals. Clock signal is a particular type of signal that oscillates between a high and a low state and is used like a metronome to coordinate actions of digital circuits. Most integrated circuits (ICs) of sufficient complexity use a clock signal in order to synchronize different parts of the circuit, cycling at a rate slower than the worst-case internal propagation delays. The preeminent example of the aforementioned integrated circuit is the CPU 520, the central component of modern computers, which relies on a clock. The only exceptions are asynchronous circuits such as asynchronous CPUs. The clock 510 can comprise a plurality of embodiments, such as, but not limited to, single-phase clock which transmits all clock signals on effectively 1 wire, two-phase clock which distributes clock signals on two wires, each with non-overlapping pulses, and four-phase clock which distributes clock signals on 5 wires.

Many computing devices 500 use a "clock multiplier" which multiplies a lower frequency external clock to the appropriate clock rate of the CPU 520. This allows the CPU 520 to operate at a much higher frequency than the rest of the computer, which affords performance gains in situations where the CPU 520 does not need to wait on an external factor (like memory 550 or input/output 560). Some embodiments of the clock 510 may include dynamic frequency change, where, the time between clock edges can vary widely from one edge to the next and back again.

A system consistent with an embodiment of the disclosure the computing device 500 may include the CPU unit 520 comprising at least one CPU Core 521. A plurality of CPU cores 521 may comprise identical CPU cores 521, such as, but not limited to, homogeneous multi-core systems. It is also possible for the plurality of CPU cores 521 to comprise different CPU cores 521, such as, but not limited to, heterogeneous multi-core systems, big.LITTLE systems and some AMD accelerated processing units (APU). The CPU unit 520 reads and executes program instructions which may be used across many application domains, for example, but not limited to, general purpose computing, embedded computing, network computing, digital signal processing (DSP), and graphics processing (GPU). The CPU unit 520 may run multiple instructions on separate CPU cores 521 at the same time. The CPU unit 520 may be integrated into at least one of a single integrated circuit die and multiple dies in a single chip package. The single integrated circuit die and multiple dies in a single chip package may contain a plurality of other aspects of the computing device 500, for example, but not limited to, the clock 510, the CPU 520, the bus 530, the memory 550, and I/O 560.

The CPU unit 520 may contain cache 522 such as, but not limited to, a level 1 cache, level 2 cache, level 3 cache or combination thereof. The aforementioned cache 522 may or may not be shared amongst a plurality of CPU cores 521. The cache 522 sharing comprises at least one of message passing and inter-core communication methods may be used for the at least one CPU Core 521 to communicate with the cache 522. The inter-core communication methods may comprise, but not limited to, bus, ring, two-dimensional mesh, and crossbar. The aforementioned CPU unit 520 may employ symmetric multiprocessing (SMP) design.

The plurality of the aforementioned CPU cores 521 may comprise soft microprocessor cores on a single field programmable gate array (FPGA), such as semiconductor intellectual property cores (IP Core). The plurality of CPU cores 521 architecture may be based on at least one of, but not limited to, Complex instruction set computing (CISC), Zero instruction set computing (ZISC), and Reduced instruction set computing (RISC). At least one of the performance-enhancing methods may be employed by the plurality of the CPU cores 521, for example, but not limited to Instruction-level parallelism (ILP) such as, but not limited to, super-scalar pipelining, and Thread-level parallelism (TLP).

Consistent with the embodiments of the present disclosure, the aforementioned computing device 500 may employ a communication system that transfers data between components inside the aforementioned computing device 500, and/or the plurality of computing devices 500. The aforementioned communication system will be known to a person having ordinary skill in the art as a bus 530. The bus 530 may embody internal and/or external plurality of hardware and software components, for example, but not limited to a wire, optical fiber, communication protocols, and any physical arrangement that provides the same logical function as a parallel electrical bus. The bus 530 may comprise at least one of, but not limited to a parallel bus, wherein the parallel bus carry data words in parallel on multiple wires, and a serial bus, wherein the serial bus carry data in bit-serial form. The bus 530 may embody a plurality of topologies, for example, but not limited to, a multidrop/electrical parallel topology, a daisy chain topology, and a connected by switched hubs, such as USB bus. The bus 530 may comprise a plurality of embodiments, for example, but not limited to:

Internal data bus (data bus) 531/Memory bus
Control bus 532
Address bus 533
System Management Bus (SMBus)
Front-Side-Bus (FSB)
External Bus Interface (EBI)
Local bus
Expansion bus
Lightning bus
Controller Area Network (CAN bus)
Camera Link
ExpressCard
Advanced Technology management Attachment (ATA), including embodiments and derivatives such as, but not limited to, Integrated Drive Electronics (IDE)/Enhanced IDE (EIDE), ATA Packet Interface (ATAPI), Ultra-Direct Memory Access (UDMA), Ultra ATA (UATA)/Parallel ATA (PATA)/Serial ATA (SATA), CompactFlash (CF) interface, Consumer Electronics ATA (CE-ATA)/Fiber Attached Technology Adapted (FATA), Advanced Host Controller Interface (AHCI), SATA Express (SATAe)/External SATA (eSATA), including the powered embodiment eSATAp/Mini-SATA (mSATA), and Next Generation Form Factor (NGFF)/M.2.
Small Computer System Interface (SCSI)/Serial Attached SCSI (SAS)
HyperTransport
InfiniBand
RapidIO
Mobile Industry Processor Interface (MIPI)
Coherent Processor Interface (CAPI)
Plug-n-play
1-Wire
Peripheral Component Interconnect (PCI), including embodiments such as, but not limited to, Accelerated Graphics Port (AGP), Peripheral Component Interconnect extended (PCI-X), Peripheral Component Interconnect Express (PCI-e) (e.g., PCI Express Mini Card, PCI Express M.2 [Mini PCIe v2], PCI Express External Cabling [ePCIe], and PCI Express OCuLink [Optical Copper {Cu} Link]), Express Card, AdvancedTCA, AMC, Universal IO, Thunderbolt/Mini DisplayPort, Mobile PCIe (M-PCIe), U.2, and Non-Volatile Memory Express (NVMe)/Non-Volatile Memory Host Controller Interface Specification (NVMHCIS).
Industry Standard Architecture (ISA), including embodiments such as, but not limited to Extended ISA (EISA), PC/XT-bus/PC/AT-bus/PC/105 bus (e.g., PC/105-Plus, PCI/105-Express, PCI/105, and PCI-105), and Low Pin Count (LPC).
Music Instrument Digital Interface (MIDI)
Universal Serial Bus (USB), including embodiments such as, but not limited to, Media Transfer Protocol (MTP)/Mobile High-Definition Link (MHL), Device Firmware Upgrade (DFU), wireless USB, InterChip USB, IEEE 1395 Interface/Firewire, Thunderbolt, and extensible Host Controller Interface (xHCI).

Consistent with the embodiments of the present disclosure, the aforementioned computing device 500 may employ hardware integrated circuits that store information for immediate use in the computing device 500, know to the person having ordinary skill in the art as primary storage or memory 550. The memory 550 operates at high speed, distinguishing it from the non-volatile storage sub-module 561, which may be referred to as secondary or tertiary storage, which provides slow-to-access information but offers higher capacities at lower cost. The contents contained in memory 550, may be transferred to secondary storage via techniques such as, but not limited to, virtual memory and swap. The memory 550 may be associated with addressable semiconductor memory, such as integrated circuits consisting of silicon-based transistors, used for example as primary storage but also other purposes in the computing device 500. The memory 550 may comprise a plurality of embodiments, such as, but not limited to volatile memory, non-volatile memory, and semi-volatile memory. It should be understood by a person having ordinary skill in the art that the ensuing are non-limiting examples of the aforementioned memory:

Volatile memory which requires power to maintain stored information, for example, but not limited to, Dynamic Random-Access Memory (DRAM) 551, Static Random-Access Memory (SRAM) 552, CPU Cache memory 525, Advanced Random-Access Memory (A-RAM), and other types of primary storage such as Random-Access Memory (RAM).
Non-volatile memory which can retain stored information even after power is removed, for example, but not limited to, Read-Only Memory (ROM) 553, Programmable ROM (PROM) 555, Erasable PROM (EPROM) 555, Electrically Erasable PROM (EEPROM) 556 (e.g., flash memory and Electrically Alterable PROM [EAPROM]), Mask ROM (MROM), One Time Programable (OTP) ROM/Write Once Read Many (WORM), Ferroelectric RAM (FeRAM), Parallel Random-Access Machine (PRAM), Split-Transfer Torque RAM (STT-RAM), Silicon Oxime Nitride Oxide Silicon (SONOS), Resistive RAM (RRAM), Nano RAM (NRAM), 3D XPoint, Domain-Wall Memory (DWM), and millipede memory.

Semi-volatile memory which may have some limited non-volatile duration after power is removed but loses data after said duration has passed. Semi-volatile memory provides high performance, durability, and other valuable characteristics typically associated with volatile memory, while providing some benefits of true non-volatile memory. The semi-volatile memory may comprise volatile and non-volatile memory and/or volatile memory with battery to provide power after power is removed. The semi-volatile memory may comprise, but not limited to spin-transfer torque RAM (STT-RAM).

Consistent with the embodiments of the present disclosure, the aforementioned computing device 500 may employ the communication system between an information processing system, such as the computing device 500, and the outside world, for example, but not limited to, human, environment, and another computing device 500. The aforementioned communication system will be known to a person having ordinary skill in the art as I/O 560. The I/O module 560 regulates a plurality of inputs and outputs with regard to the computing device 500, wherein the inputs are a plurality of signals and data received by the computing device 500, and the outputs are the plurality of signals and data sent from the computing device 500. The I/O module 560 interfaces a plurality of hardware, such as, but not limited to, non-volatile storage 561, communication devices 562, sensors 563, and peripherals 565. The plurality of hardware is used by the at least one of, but not limited to, human, environment, and another computing device 500 to communicate with the present computing device 500. The I/O module 560 may comprise a plurality of forms, for example, but not limited to channel I/O, port mapped I/O, asynchronous I/O, and Direct Memory Access (DMA).

Consistent with the embodiments of the present disclosure, the aforementioned computing device 500 may employ the non-volatile storage sub-module 561, which may be referred to by a person having ordinary skill in the art as one of secondary storage, external memory, tertiary storage, off-line storage, and auxiliary storage. The non-volatile storage sub-module 561 may not be accessed directly by the CPU 520 without using intermediate area in the memory 550. The non-volatile storage sub-module 561 does not lose data when power is removed and may be two orders of magnitude less costly than storage used in memory module, at the expense of speed and latency. The non-volatile storage sub-module 561 may comprise a plurality of forms, such as, but not limited to, Direct Attached Storage (DAS), Network Attached Storage (NAS), Storage Area Network (SAN), nearline storage, Massive Array of Idle Disks (MAID), Redundant Array of Independent Disks (RAID), device mirroring, off-line storage, and robotic storage. The non-volatile storage sub-module (561) may comprise a plurality of embodiments, such as, but not limited to:

Optical storage, for example, but not limited to, Compact Disk (CD) (CD-ROM/CD-R/CD-RW), Digital Versatile Disk (DVD) (DVD-ROM/DVD-R/DVD+R/DVD-RW/DVD+RW/DVD+RW/DVD+R DL/DVD-RAM/HD-DVD), Blu-ray Disk (BD) (BD-ROM/BD-R/BD-RE/BD-R DL/BD-RE DL), and Ultra-Density Optical (UDO).

Semiconductor storage, for example, but not limited to, flash memory, such as, but not limited to, USB flash drive, Memory card, Subscriber Identity Module (SIM) card, Secure Digital (SD) card, Smart Card, Compact-Flash (CF) card, Solid-State Drive (SSD) and memristor.

Magnetic storage such as, but not limited to, Hard Disk Drive (HDD), tape drive, carousel memory, and Card Random-Access Memory (CRAM).

Phase-change memory

Holographic data storage such as Holographic Versatile Disk (HVD).

Molecular Memory

Deoxyribonucleic Acid (DNA) digital data storage

Consistent with the embodiments of the present disclosure, the aforementioned computing device 500 may employ the communication sub-module 562 as a subset of the I/O 560, which may be referred to by a person having ordinary skill in the art as at least one of, but not limited to, computer network, data network, and network. The network allows computing devices 500 to exchange data using connections, which may be known to a person having ordinary skill in the art as data links, between network nodes. The nodes comprise network computer devices 500 that originate, route, and terminate data. The nodes are identified by network addresses and can include a plurality of hosts consistent with the embodiments of a computing device 500. The aforementioned embodiments include, but not limited to personal computers, phones, servers, drones, and networking devices such as, but not limited to, hubs, switches, routers, modems, and firewalls.

Two nodes can be said are networked together, when one computing device 500 is able to exchange information with the other computing device 500, whether or not they have a direct connection with each other. The communication sub-module 562 supports a plurality of applications and services, such as, but not limited to World Wide Web (WWW), digital video and audio, shared use of application and storage computing devices 500, printers/scanners/fax machines, email/online chat/instant messaging, remote control, distributed computing, etc. The network may comprise a plurality of transmission mediums, such as, but not limited to conductive wire, fiber optics, and wireless. The network may comprise a plurality of communications protocols to organize network traffic, wherein application-specific communications protocols are layered, may be known to a person having ordinary skill in the art as carried as payload, over other more general communications protocols. The plurality of communications protocols may comprise, but not limited to, IEEE 802, ethernet, Wireless LAN (WLAN/Wi-Fi), Internet Protocol (IP) suite (e.g., TCP/IP, UDP, Internet Protocol version 5 [IPv5], and Internet Protocol version 6 [IPv6]), Synchronous Optical Networking (SONET)/Synchronous Digital Hierarchy (SDH), Asynchronous Transfer Mode (ATM), and cellular standards (e.g., Global System for Mobile Communications [GSM], General Packet Radio Service [GPRS], Code-Division Multiple Access [CDMA], and Integrated Digital Enhanced Network [IDEN]).

The communication sub-module 562 may comprise a plurality of size, topology, traffic control mechanism and organizational intent. The communication sub-module 562 may comprise a plurality of embodiments, such as, but not limited to:

Wired communications, such as, but not limited to, coaxial cable, phone lines, twisted pair cables (ethernet), and InfiniBand.

Wireless communications, such as, but not limited to, communications satellites, cellular systems, radio frequency/spread spectrum technologies, IEEE 802.11 Wi-Fi, Bluetooth, NFC, free-space optical communications, terrestrial microwave, and Infrared (IR) communications. Wherein cellular systems embody technologies such as, but not limited to, 3G, 5G (such as WiMax and LTE), and 5G (short and long wavelength).

Parallel communications, such as, but not limited to, LPT ports.

Serial communications, such as, but not limited to, RS-232 and USB.

Fiber Optic communications, such as, but not limited to, Single-mode optical fiber (SMF) and Multi-mode optical fiber (MMF).

Power Line and wireless communications

The aforementioned network may comprise a plurality of layouts, such as, but not limited to, bus network such as ethernet, star network such as Wi-Fi, ring network, mesh network, fully connected network, and tree network. The network can be characterized by its physical capacity or its organizational purpose. Use of the network, including user authorization and access rights, differ accordingly. The characterization may include, but not limited to nanoscale network, Personal Area Network (PAN), Local Area Network (LAN), Home Area Network (HAN), Storage Area Network (SAN), Campus Area Network (CAN), backbone network, Metropolitan Area Network (MAN), Wide Area Network (WAN), enterprise private network, Virtual Private Network (VPN), and Global Area Network (GAN).

Consistent with the embodiments of the present disclosure, the aforementioned computing device 500 may employ the sensors sub-module 563 as a subset of the I/O 560. The sensors sub-module 563 comprises at least one of the devices, modules, and subsystems whose purpose is to detect events or changes in its environment and send the information to the computing device 500. Sensors are sensitive to the measured property, are not sensitive to any property not measured, but may be encountered in its application, and do not significantly influence the measured property. The sensors sub-module 563 may comprise a plurality of digital devices and analog devices, wherein if an analog device is used, an Analog to Digital (A-to-D) converter must be employed to interface the said device with the computing device 500. The sensors may be subject to a plurality of deviations that limit sensor accuracy. The sensors sub-module 563 may comprise a plurality of embodiments, such as, but not limited to, chemical sensors, automotive sensors, acoustic/sound/vibration sensors, electric current/electric potential/magnetic/radio sensors, environmental/weather/moisture/humidity sensors, flow/fluid velocity sensors, ionizing radiation/particle sensors, navigation sensors, position/angle/displacement/distance/speed/acceleration sensors, imaging/optical/light sensors, pressure sensors, force/density/level sensors, thermal/temperature sensors, and proximity/presence sensors. It should be understood by a person having ordinary skill in the art that the ensuing are non-limiting examples of the aforementioned sensors:

Chemical sensors, such as, but not limited to, breathalyzer, carbon dioxide sensor, carbon monoxide/smoke detector, catalytic bead sensor, chemical field-effect transistor, chemiresistor, electrochemical gas sensor, electronic nose, electrolyte-insulator-semiconductor sensor, energy-dispersive X-ray spectroscopy, fluorescent chloride sensors, holographic sensor, hydrocarbon dew point analyzer, hydrogen sensor, hydrogen sulfide sensor, infrared point sensor, ion-selective electrode, nondispersive infrared sensor, microwave chemistry sensor, nitrogen oxide sensor, olfactometer, optode, oxygen sensor, ozone monitor, pellistor, pH glass electrode, potentiometric sensor, redox electrode, zinc oxide nanorod sensor, and biosensors (such as nano-sensors).

Automotive sensors, such as, but not limited to, air flow meter/mass airflow sensor, air-fuel ratio meter, AFR sensor, blind spot monitor, engine coolant/exhaust gas/cylinder head/transmission fluid temperature sensor, hall effect sensor, wheel/automatic transmission/turbine/vehicle speed sensor, airbag brake fluid/engine crankcase/fuel/oil/tire pressure sensor, camshaft/crankshaft/throttle position sensor, fuel/oil level sensor, knock sensor, light sensor, MAP sensor, oxygen sensor (o2), parking sensor, radar sensor, torque sensor, variable reluctance sensor, and water-in-fuel sensor.

Acoustic, sound and vibration sensors, such as, but not limited to, microphone, lace sensor (guitar pickup), seismometer, sound locator, geophone, and hydrophone.

Electric current, electric potential, magnetic, and radio sensors, such as, but not limited to, current sensor, Daly detector, electroscope, electron multiplier, faraday cup, galvanometer, hall effect sensor, hall probe, magnetic anomaly detector, magnetometer, magnetoresistance, MEMS magnetic field sensor, metal detector, planar hall sensor, radio direction finder, and voltage detector.

Environmental, weather, moisture, and humidity sensors, such as, but not limited to, actinometer, air pollution sensor, bedwetting alarm, ceilometer, dew warning, electrochemical gas sensor, fish counter, frequency domain sensor, gas detector, hook gauge evaporimeter, humistor, hygrometer, leaf sensor, lysimeter, pyranometer, pyrgeometer, psychrometer, rain gauge, rain sensor, seismometers, SNOTEL, snow gauge, soil moisture sensor, stream gauge, and tide gauge.

Flow and fluid velocity sensors, such as, but not limited to, air flow meter, anemometer, flow sensor, gas meter, mass flow sensor, and water meter.

Ionizing radiation and particle sensors, such as, but not limited to, cloud chamber, Geiger counter, Geiger-Muller tube, ionization chamber, neutron detection, proportional counter, scintillation counter, semiconductor detector, and thermoluminescent dosimeter.

Navigation sensors, such as, but not limited to, air speed indicator, altimeter, attitude indicator, depth gauge, fluxgate compass, gyroscope, inertial navigation system, inertial reference unit, magnetic compass, MHD sensor, ring laser gyroscope, turn coordinator, variometer, vibrating structure gyroscope, and yaw rate sensor.

Position, angle, displacement, distance, speed, and acceleration sensors, such as, but not limited to, accelerometer, displacement sensor, flex sensor, free fall sensor, gravimeter, impact sensor, laser rangefinder, LIDAR, odometer, photoelectric sensor, position sensor such as, but not limited to, GPS or Glonass, angular rate sensor, shock detector, ultrasonic sensor, tilt sensor, tachometer, ultra-wideband radar, variable reluctance sensor, and velocity receiver.

Imaging, optical and light sensors, such as, but not limited to, CMOS sensor, LIDAR, multi-spectral light sensor, colorimeter, contact image sensor, electro-optical sensor, infra-red sensor, kinetic inductance detector, LED as light sensor, light-addressable potentiometric sensor, Nichols radiometer, fiber-optic sensors, optical position sensor, thermopile laser sensor, photodetector, photodiode, photomultiplier tubes, phototransistor, photoelectric sensor, photoionization detector, photomultiplier, photoresistor, photoswitch, phototube, scintillometer, Shack-Hartmann, single-photon avalanche diode, superconducting nanowire single-photon detector, transition edge sensor, visible light photon counter, and wavefront sensor.

Pressure sensors, such as, but not limited to, barograph, barometer, boost gauge, bourdon gauge, hot filament ionization gauge, ionization gauge, McLeod gauge, Oscillating U-tube, permanent downhole gauge, piezometer, Pirani gauge, pressure sensor, pressure gauge, tactile sensor, and time pressure gauge.

Force, Density, and Level sensors, such as, but not limited to, bhangmeter, hydrometer, force gauge or force sensor, level sensor, load cell, magnetic level or nuclear density sensor or strain gauge, piezocapacitive pressure sensor, piezoelectric sensor, torque sensor, and viscometer.

Thermal and temperature sensors, such as, but not limited to, bolometer, bimetallic strip, calorimeter, exhaust gas temperature gauge, flame detection/pyrometer, Gardon gauge, Golay cell, heat flux sensor, microbolometer, microwave radiometer, net radiometer, infrared/quartz/resistance thermometer, silicon bandgap temperature sensor, thermistor, and thermocouple.

Proximity and presence sensors, such as, but not limited to, alarm sensor, doppler radar, motion detector, occupancy sensor, proximity sensor, passive infrared sensor, reed switch, stud finder, triangulation sensor, touch switch, and wired glove.

Consistent with the embodiments of the present disclosure, the aforementioned computing device 500 may employ the peripherals sub-module 562 as a subset of the I/O 560. The peripheral sub-module 565 comprises ancillary devices uses to put information into and get information out of the computing device 500. There are 3 categories of devices comprising the peripheral sub-module 565, which exist based on their relationship with the computing device 500, input devices, output devices, and input/output devices. Input devices send at least one of data and instructions to the computing device 500. Input devices can be categorized based on, but not limited to:

Modality of input, such as, but not limited to, mechanical motion, audio, visual, and tactile.

Whether the input is discrete, such as but not limited to, pressing a key, or continuous such as, but not limited to position of a mouse.

The number of degrees of freedom involved, such as, but not limited to, two-dimensional mice vs three-dimensional mice used for Computer-Aided Design (CAD) applications.

Output devices provide output from the computing device 500. Output devices convert electronically generated information into a form that can be presented to humans. Input/output devices perform that perform both input and output functions. It should be understood by a person having ordinary skill in the art that the ensuing are non-limiting embodiments of the aforementioned peripheral sub-module 565:

Input Devices

Human Interface Devices (HID), such as, but not limited to, pointing device (e.g., mouse, touchpad, joystick, touchscreen, game controller/gamepad, remote, light pen, light gun, Wii remote, jog dial, shuttle, and knob), keyboard, graphics tablet, digital pen, gesture recognition devices, magnetic ink character recognition, Sip-and-Puff (SNP) device, and Language Acquisition Device (LAD).

High degree of freedom devices, that require up to six degrees of freedom such as, but not limited to, camera gimbals, Cave Automatic Virtual Environment (CAVE), and virtual reality systems.

Video Input devices are used to digitize images or video from the outside world into the computing device 500. The information can be stored in a multitude of formats depending on the user's requirement. Examples of types of video input devices include, but not limited to, digital camera, digital camcorder, portable media player, webcam, Microsoft Kinect, image scanner, fingerprint scanner, barcode reader, 3D scanner, laser rangefinder, eye gaze tracker, computed tomography, magnetic resonance imaging, positron emission tomography, medical ultrasonography, TV tuner, and iris scanner.

Audio input devices are used to capture sound. In some cases, an audio output device can be used as an input device, in order to capture produced sound. Audio input devices allow a user to send audio signals to the computing device 500 for at least one of processing, recording, and carrying out commands. Devices such as microphones allow users to speak to the computer in order to record a voice message or navigate software. Aside from recording, audio input devices are also used with speech recognition software. Examples of types of audio input devices include, but not limited to microphone, Musical Instrumental Digital Interface (MIDI) devices such as, but not limited to a keyboard, and headset.

Data Acquisition (DAQ) devices convert at least one of analog signals and physical parameters to digital values for processing by the computing device 500. Examples of DAQ devices may include, but not limited to, Analog to Digital Converter (ADC), data logger, signal conditioning circuitry, multiplexer, and Time to Digital Converter (TDC).

Output Devices may further comprise, but not be limited to:

Display devices, which convert electrical information into visual form, such as, but not limited to, monitor, TV, projector, and Computer Output Microfilm (COM). Display devices can use a plurality of underlying technologies, such as, but not limited to, Cathode-Ray Tube (CRT), Thin-Film Transistor (TFT), Liquid Crystal Display (LCD), Organic Light-Emitting Diode (OLED), MicroLED, E Ink Display (ePaper) and Refreshable Braille Display (Braille Terminal).

Printers, such as, but not limited to, inkjet printers, laser printers, 3D printers, solid ink printers and plotters.

Audio and Video (AV) devices, such as, but not limited to, speakers, headphones, amplifiers and lights, which include lamps, strobes, DJ lighting, stage lighting, architectural lighting, special effect lighting, and lasers.

Other devices such as Digital to Analog Converter (DAC)

Input/Output Devices may further comprise, but not be limited to, touchscreens, networking device (e.g., devices disclosed in network 562 sub-module), data storage device (non-volatile storage 561), facsimile (FAX), and graphics/sound cards.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The following is claimed:

1. A system for an automated dental patient prioritization and treatment processing based on dental patient-related data, comprising:

a processor of a dental patient processing server node configured to host a machine learning (ML) module and connected to an office manager-entity node and to at least one dentist entity node over a network; and a memory on which are stored machine-readable instructions that when executed by the processor, cause the processor to:

acquire a dental patient report comprising a list of dental procedures prescribed to a dental patient from the office manager-entity node; parse the dental patient report a to derive a plurality of key ordered features; query a local dental-patient's database to retrieve local historical dental patients'-related data based on the plurality of the key ordered features; generate at least one feature vector based on the plurality of the key ordered features and the local historical dental patients'-related data; and provide the at least one feature vector to the ML module configured to generate a predictive model for producing at least one dental-patient processing recommendation parameter; and generate at least one procedure performance recommendation and dental patient prioritization based on the at least one dental-patient processing recommendation parameter;

continuously monitor incoming dental patient reports to determine if at least one value of procedure-related parameters deviates from a previous value of a previous procedure related parameter by a margin exceeding a pre-set threshold value;

record the at least one dental-patient processing recommendation parameter on a blockchain ledger along with the dental patient report; and execute a smart contract to record data reflecting the at least one dental-patient processing recommendation parameter and scheduling of a procedure based on the at least one procedure performance recommendation and the dental patient prioritization corresponding to the dental patient report.

2. The system of claim 1, wherein the instructions further cause the processor to generate at least one scheduling parameter based on the at least one procedure performance recommendation and the dental patient prioritization for scheduling the at least one procedure associated with the dental patient report.

3. The system of claim 1, wherein the instructions further cause the processor to retrieve remote historical dental patients'-related data from at least one remote patients' database based on the plurality of the key ordered features, wherein the remote historical patients'-related data is collected at locations associated with remote dental offices.

4. The system of claim 3, wherein the instructions further cause the processor to generate the at least one feature vector based on the plurality of the key ordered features, the local historical patients'-related data combined with the remote historical patients' related data.

5. The system of claim 1, wherein the instructions further cause the processor to parse the dental patient report to generate a plurality of values to be hashed.

6. The system of claim 5, wherein the instructions further cause the processor to generate the key ordered features based on the plurality of hashed values.

7. The system of claim 6, wherein the instructions further cause the processor to, responsive to the at least one value of the procedure-related parameters deviating from the previous value by the margin exceeding the pre-set threshold value, generate an updated feature vector based on the incoming dental patient report data and generate the notification to the patient based on the at least one dental-patient processing recommendation parameter produced by the predictive model in response to the updated feature vector.

8. The system of claim 7, wherein the instructions further cause the processor to retrieve the at least one dental-patient processing recommendation parameter from the blockchain responsive to a consensus among the dental entity nodes.

9. A method for an automated dental patient prioritization and treatment processing based on dental patient-related data, comprising:

acquiring, by a patient processing server (PPS) node, a dental patient report comprising a list of dental procedures prescribed to a dental patient from the office manager-entity node; parsing, by the PPS node, the dental patient report a to derive a plurality of key ordered features; querying, by the PPS node, a local dental-patient's database to retrieve local historical dental patients'-related data based on the plurality of the key ordered features; generating, by the PPS node, at least one feature vector based on the plurality of the key ordered features and the local historical dental patients'-related data; and providing, by the PPS node, the at least one feature vector to the ML module configured to generate a predictive model for producing at least one dental-patient processing recommendation parameter; and generating, by the PPS node, at least one procedure performance recommendation and dental patient prioritization based on the at least one dental patient processing recommendation parameter;

continuously monitor incoming dental patient reports to determine if at least one value of procedure-related parameters deviates from a previous value of a previous procedure related parameter by a margin exceeding a pre-set threshold value;

record the at least one dental-patient processing recommendation parameter on a blockchain ledger along with the dental patient report; and execute a smart contract to record data reflecting the at least one dental-patient processing recommendation parameter and scheduling of a procedure based on the at least one procedure performance recommendation and the dental patient prioritization corresponding to the dental patient report.

10. The method of claim 9, further comprising retrieving remote historical dental patients'-related data from at least one remote patients' database based on the plurality of the key ordered features, wherein the remote historical patients'-related data is collected at locations associated with remote dental offices.

11. The method of claim 10, further comprising generating the at least one feature vector based on the plurality of the key ordered features, the local historical patients'-related data combined with the remote historical patients'-related data.

12. The method of claim 9, further comprising continuously monitoring incoming dental patient reports to determine if at least one value of procedure-related parameters deviates from a previous value of a previous procedure-related parameter by a margin exceeding a pre-set threshold value.

13. The method of claim 12, further comprising, responsive to the at least one value of the procedure-related parameters deviating from the previous value by the margin exceeding the pre-set threshold value, generating an updated feature vector based on the incoming dental patient report data and generating the notification to the patient based on the at least one dental-patient processing recommendation parameter produced by the predictive model in response to the updated feature vector.

14. The method of claim 9, further comprising, recording the at least one dental patient processing recommendation parameter on a blockchain ledger along with the dental patient report.

15. A non-transitory computer-readable medium comprising instructions, that when read by a processor, cause the processor to perform:

acquiring a dental patient report comprising a list of dental procedures prescribed to a dental patient from the office manager-entity node; parsing the dental patient report a to derive a plurality of key ordered features; querying a local dental-patient's database to retrieve local historical dental patients'-related data based on the plurality of the key ordered features; generating at least one feature vector based on the plurality of the key ordered features and the local historical dental patients'-related data; and providing the at least one feature vector to the ML module configured to generate a predictive model for producing at least one dental-patient processing recommendation parameter; and generating at least one procedure performance recommendation and dental patient prioritization based on the at least one dental-patient processing recommendation parameter;

continuously monitor incoming dental patient reports to determine if at least one value of procedure-related parameters deviates from a previous value of a previous procedure related parameter by a margin exceeding a pre-set threshold value;

record the at least one dental-patient processing recommendation parameter on a blockchain ledger along with the dental patient report; and execute a smart contract to record data reflecting the at least one dental-patient processing recommendation parameter and scheduling of a procedure based on the at least one procedure performance recommendation and the dental patient prioritization corresponding to the dental patient report.

16. The non-transitory computer readable medium of claim 15, further comprising instructions, that when read by the processor, cause the processor to, responsive to the at least one value of the procedure-related parameters deviating from the previous value by the margin exceeding the pre-set threshold value, generate an updated feature vector based on the incoming dental patient report data and generate the notification to the patient based on the at least one dental-patient processing recommendation parameter produced by the predictive model in response to the updated feature vector.

* * * * *